(12) United States Patent
Sina Raja et al.

(10) Patent No.: US 12,295,617 B2
(45) Date of Patent: *May 13, 2025

(54) RELEASABLE FLUID CONTROLLER AND INSEMINATION DEVICE

(71) Applicant: Hannah Life Technologies PTE, Ltd., Singapore (SG)

(72) Inventors: Prusothman M. Sina Raja, Singapore (SG); Chee Keong Tee, Singapore (SG); Zongyuan Xu, Signapore (SG); Qi Tan, Singapore (SG); Chelsea Nisban, Singapore (SG); Ziyue Lu, Singapore (SG); Kelli Zhao Rong Chan, Singapore (SG)

(73) Assignee: HANNAH LIFE TECHNOLOGIES PTE, LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,508

(22) Filed: Apr. 19, 2023

(65) Prior Publication Data

US 2023/0277219 A1    Sep. 7, 2023

Related U.S. Application Data

(63) Continuation of application No. 18/061,532, filed on Dec. 5, 2022.
(Continued)

(51) Int. Cl.
*A61B 17/43*    (2006.01)
*A61D 19/02*    (2006.01)
(Continued)

(52) U.S. Cl.
CPC ............ *A61B 17/43* (2013.01); *A61D 19/027* (2013.01); *A61M 5/3148* (2013.01);
(Continued)

(58) Field of Classification Search
CPC ....... A61B 17/42; A61B 17/425; A61B 17/43; A61D 19/027; A61D 19/028
See application file for complete search history.

(56) References Cited

U.S. PATENT DOCUMENTS

| | | | |
|---|---|---|---|
| 2004/0071679 A1* | 4/2004 | De Simone | A61P 15/02 424/93.45 |
| 2017/0189649 A1* | 7/2017 | Anderson | A61M 25/06 |
| 2019/0282271 A1* | 9/2019 | Plessala | A61B 17/43 |

FOREIGN PATENT DOCUMENTS

| | | | | |
|---|---|---|---|---|
| FR | 2889052 | * | 2/2007 | ........... A61D 19/027 |
| KR | 20170029052 | * | 3/2017 | ........... A61D 19/027 |

* cited by examiner

*Primary Examiner* — Carrie R Dorna
(74) *Attorney, Agent, or Firm* — FINNEGAN, HENDERSON, FARABOW, GARRETT & DUNNER LLP

(57) ABSTRACT

Disclosed are fluid controllers configured for removable attachment to a fluid introduction device, wherein the fluid controller comprises a body configured to extend at least partially over the fluid introduction device; an orifice arranged relative to the body to facilitate transfer of a fluid from the fluid introduction device through the fluid controller; a fluid retention structure extending outwardly from at least a portion of the body, wherein the fluid retention structure is configured to engage with a wall of a vaginal canal and inhibit a flow of the fluid from the vaginal canal; and at least one connector configured to releasably attach the fluid controller to the fluid introduction device.

39 Claims, 16 Drawing Sheets

Related U.S. Application Data

(60) Provisional application No. 63/358,321, filed on Jul. 5, 2022, provisional application No. 63/362,601, filed on Apr. 7, 2022, provisional application No. 63/317,213, filed on Mar. 7, 2022.

(51) Int. Cl.
*A61M 5/31* (2006.01)
*A61M 31/00* (2006.01)

(52) U.S. Cl.
CPC .............. *A61M 2005/3103* (2013.01); *A61M 2005/3142* (2013.01); *A61M 31/00* (2013.01)

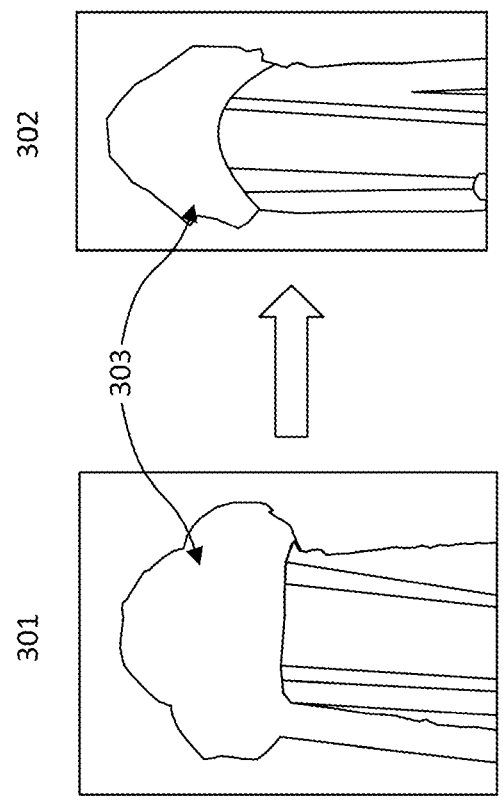
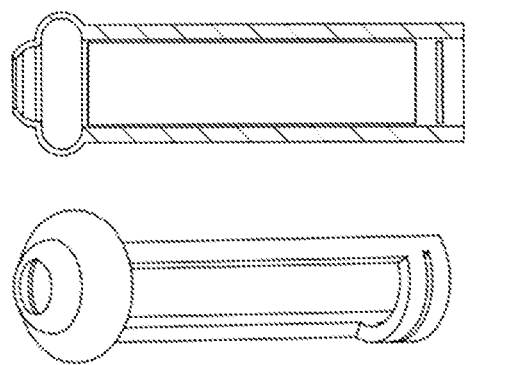
FIG. 3

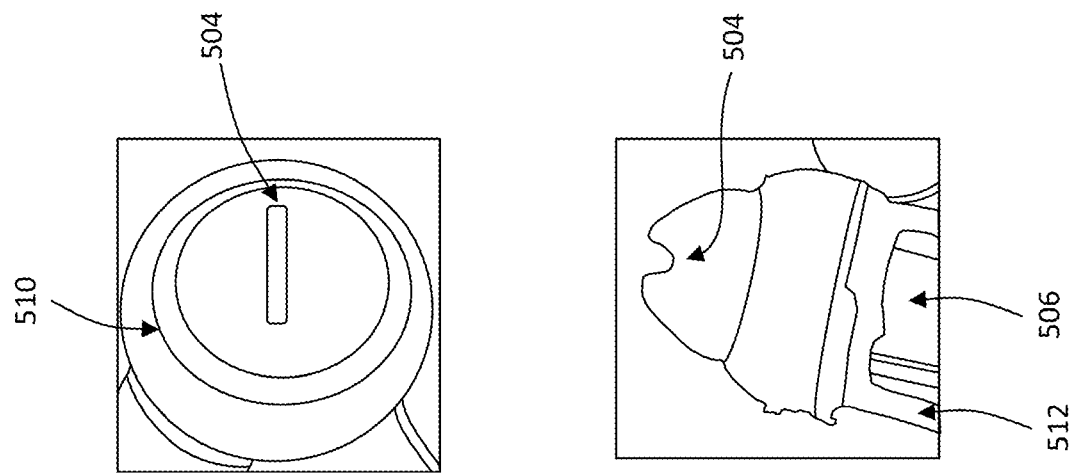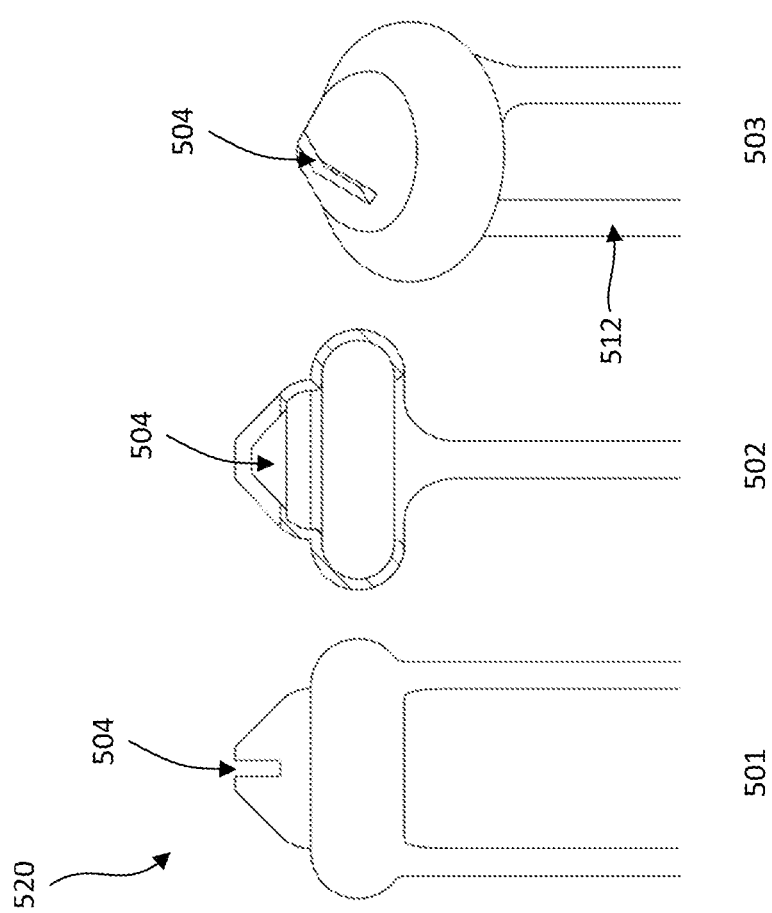
FIG. 5

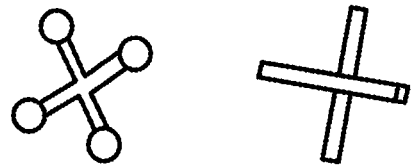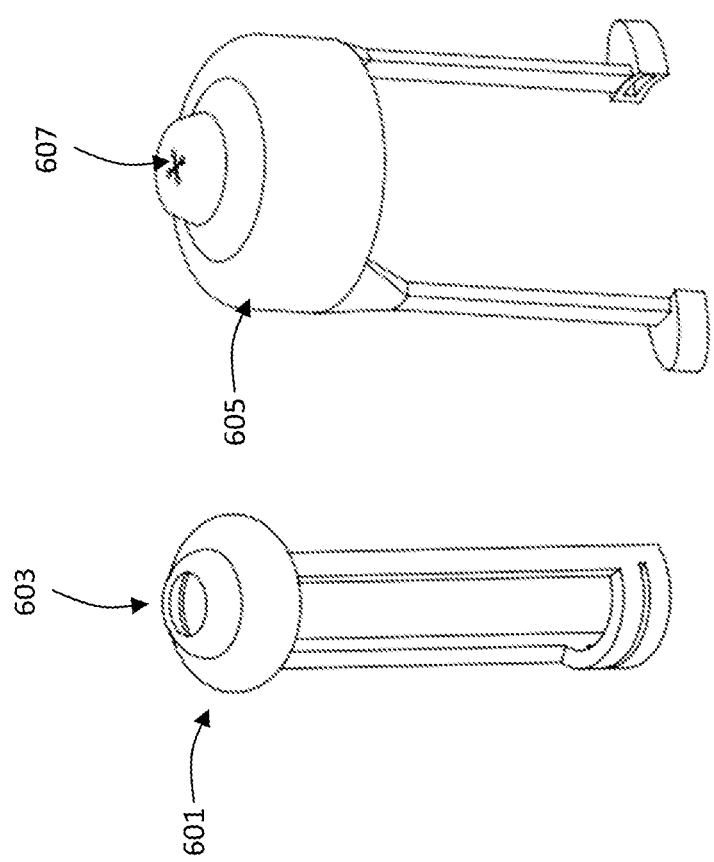
FIG. 6

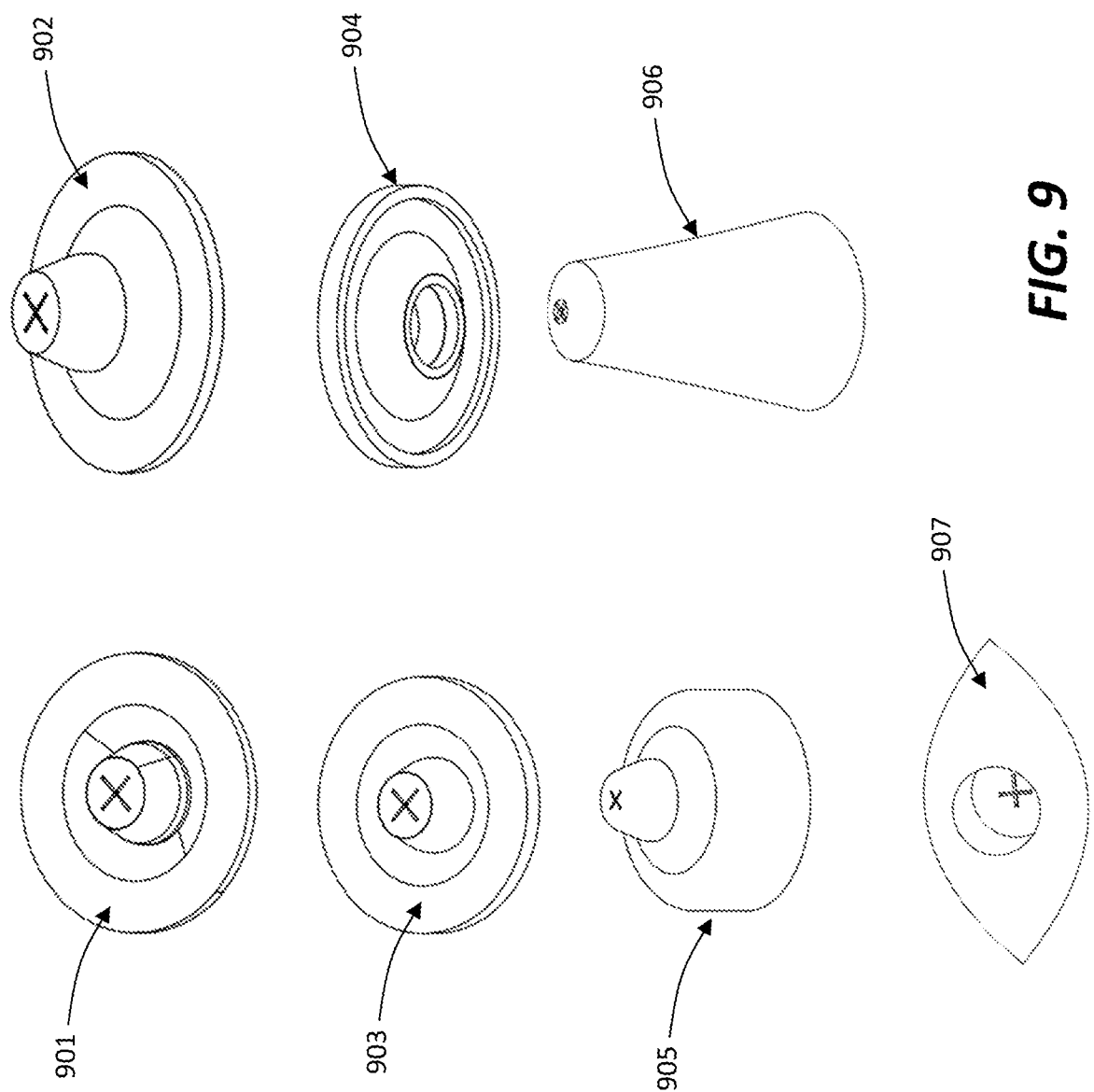

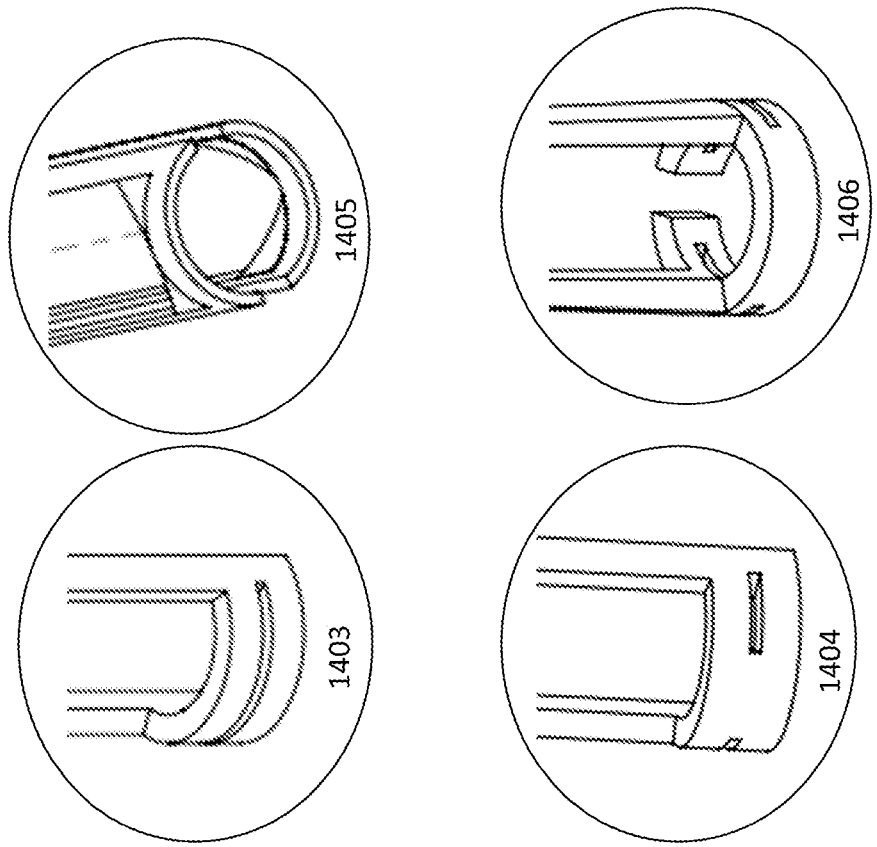
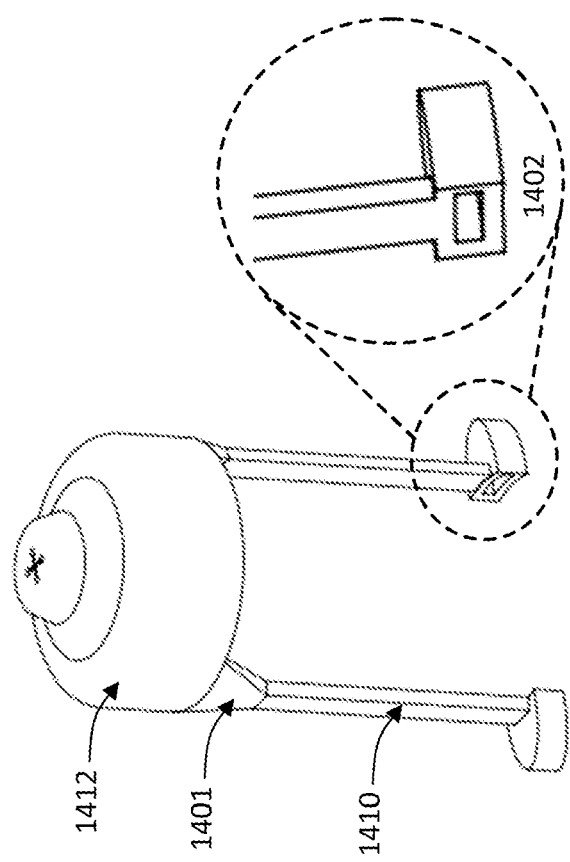
FIG. 14

RELEASABLE FLUID CONTROLLER AND INSEMINATION DEVICE

This application is a continuation of Ser. No. 18/061,532, filed Dec. 5, 2022 which claims the benefit of priority of U.S. Provisional Patent Application No. 63/317,213, filed on Mar. 7, 2022, U.S. Provisional Patent Application No. 63/362,601, filed on Apr. 7, 2022, and U.S. Provisional Patent Application No. 63/358,321, filed on Jul. 5, 2022. Each of these applications is hereby incorporated herein by reference in its entirety.

BACKGROUND

Infertility is a common condition that affects as many as one in six couples trying to conceive. While causes of infertility may vary, nearly 60% of infertility is attributable to low sperm count or motility. Several infertility treatments such as medications to assist with hormone balance and/or ovulation, intrauterine insemination (IUI), and in vitro fertilization (IVF) are invasive, often accompanied by undesirable side effects, and may be prohibitively expensive for those seeking infertility treatment.

There is a need for new and improved devices and methods for providing people with a safe, easy, and affordable treatment that can be used on a frequent basis to increase the overall likelihood of a successful pregnancy. The disclosed devices and methods are aimed at addresses one or more of these challenges. For example, the disclosed methods and fluid introduction systems may provide benefits for any application where there may be a desire to introduce fluid into a volume and then retain, or partially retain, that fluid in the volume over time. In some applications, the disclosed systems and methods are aimed at promoting conception.

SUMMARY

Disclosed are insemination devices comprising a fluid controller and a fluid introduction device, wherein the fluid controller is configured for removable attachment to the fluid introduction device. For example, the disclosed fluid controllers may include a body configured to extend at least partially over the fluid introduction device (e.g., a syringe or other fluid carrier). The fluid controller may further include an orifice arranged relative to the body to facilitate transfer of a fluid from the fluid introduction device through the fluid controller; a fluid retention structure extending outwardly from at least a portion of the body, wherein the fluid retention structure is configured to engage with a wall of a vaginal canal and inhibit a flow of the fluid from the vaginal canal; and at least one connector configured to releasably attach the fluid controller to the fluid introduction device. Also described are methods for potentially aiding conception using the disclosed insemination devices.

In some embodiments, the fluid retention structure is configured such that attachment of the fluid controller to the fluid introduction device causes a reduction in at least one dimension associated with the fluid retention structure. In some embodiments, the at least one dimension includes a radial dimension.

In some embodiments, the at least one connector is further configured such that the fluid controller can be detached from the fluid introduction device after insertion into the vaginal canal and the fluid introduction device can be removed from the vaginal canal without removal of the fluid controller from the vaginal canal.

In some embodiments, the fluid retention structure is configured to expand in at least one dimension upon detachment of the fluid controller from the fluid introduction device.

In some embodiments, the fluid introduction device comprises a syringe.

In some embodiments, the fluid retention structure has a maximal cross-sectional diameter ranging from 12 mm to 50 mm when the fluid controller is not attached to the fluid introduction device.

In some embodiments, the fluid controller is configured such that the maximal cross-sectional diameter of the fluid retention structure is reduced when the fluid controller is attached to the fluid introduction device.

In some embodiments, the fluid retention structure has a Shore A hardness ranging from 0 to 70.

In some embodiments, the fluid retention structure comprises one or more of a flap, a bulb, a plug, or a valve.

In some embodiments, the fluid retention structure comprises a plug.

In some embodiments, the fluid retention structure comprises at least two flaps.

In some embodiments, the at least one connector comprises one or more of a loop, a notch, a slot, a hook, or a ridge.

In some embodiments, the at least one connector is configured to receive a protrusion associated with the fluid introduction device.

In some embodiments, the fluid controller comprises silicone.

In some embodiments, the fluid controller comprises from 10 weight percent to 100 weight percent silicone by total weight of the fluid controller.

In some embodiments, the fluid retention structure is configured to engage the vaginal wall and retain the fluid controller at least partially within the vaginal canal after the fluid introduction device is detached from the fluid controller and removed from the vaginal canal.

In some embodiments, a coefficient of friction between the fluid controller and the vaginal wall is greater than a coefficient of friction between the fluid controller and the fluid introduction device.

In some embodiments, the orifice comprises at least two intersecting slots.

In some embodiments, the at least one connector comprises at least one elastic segment configured to stretch when the fluid controller is attached to the fluid introduction device.

In some embodiments, at least a portion of the fluid controller comprises a thermally responsive material configured to change shape or color when at least partially within the vaginal canal.

In some embodiments, at least a portion of the fluid controller comprises a pH responsive material configured to change shape or color when at least partially within the vaginal canal.

In some embodiments, at least a portion of the fluid controller comprises a moisture responsive material configured to change shape or color after introduction at least partially within the vaginal canal.

In some embodiments, the fluid introduction device is a syringe comprising a barrel flange, and the at least one connector is configured to removably attach to a portion of the barrel flange.

In some embodiments, the fluid controller further includes a quick release element configured to facilitate detachment of the fluid controller from the fluid introduction device.

In some embodiments, the fluid controller further includes one or more alignment guides configured to orient the fluid controller relative to the fluid introduction device.

In some embodiments, the fluid includes semen.

In some embodiments, the fluid includes at least one pharmaceutical product.

In some embodiments, the fluid includes progesterone.

Also disclosed are methods for aiding conception using the disclosed insemination devices.

BRIEF DESCRIPTION OF THE DRAWINGS

FIG. 3 depicts an exemplary fluid controller in both a relaxed state and a deformed state.

FIG. 5 depicts an exemplary fluid retention structure and orifice embodiment.

FIG. 6 depicts exemplary orifice embodiments.

FIG. 9 depicts exemplary fluid retention structure embodiments.

FIG. 14 depicts exemplary connector embodiments for attaching a fluid controller to a fluid introduction device.

DETAILED DESCRIPTION

Figure 1:
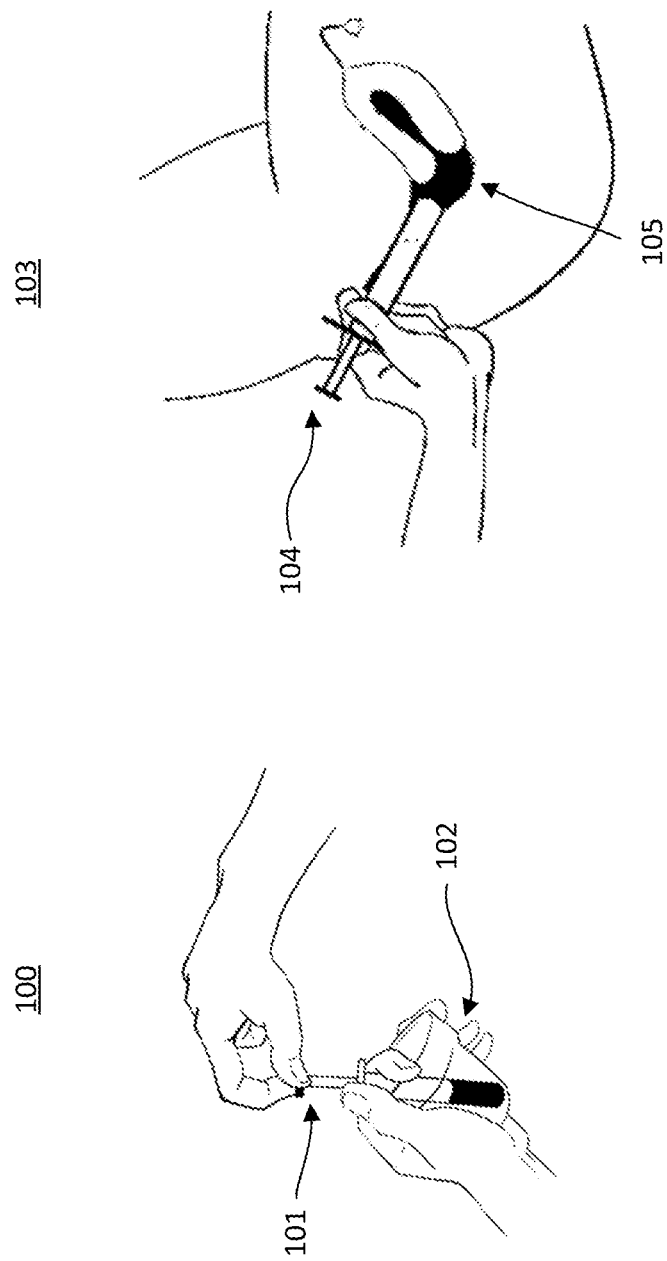
FIG. 1 depicts a cup and syringe insemination method.

FIG. 1 provides an overview of an insemination technique for introducing semen into a vaginal cavity. For example, at step 100, ejaculate is collected in a cup 102 and drawn into a syringe 101. Next, the syringe 101 is positioned within the vaginal canal where the ejaculate is deposited 105. While this technique can be effective in promoting conception, in some cases, the ejaculate may be free to exit the vaginal canal once syringe 101 is removed. Even prior to removal of the syringe, the ejaculate may leak out of the vaginal canal through a gap between the syringe barrel and the vaginal wall. Further, leaving the syringe within the vaginal canal for extended periods of time may cause discomfort for the user.

The disclosed insemination devices are aimed at improving conception by promoting ejaculate retention within a vaginal canal (or by reducing ejaculate leakage from the vaginal canal). The disclosed insemination devices may include or may be used in conjunction with various types of fluid introduction devices.

Figure 2A:
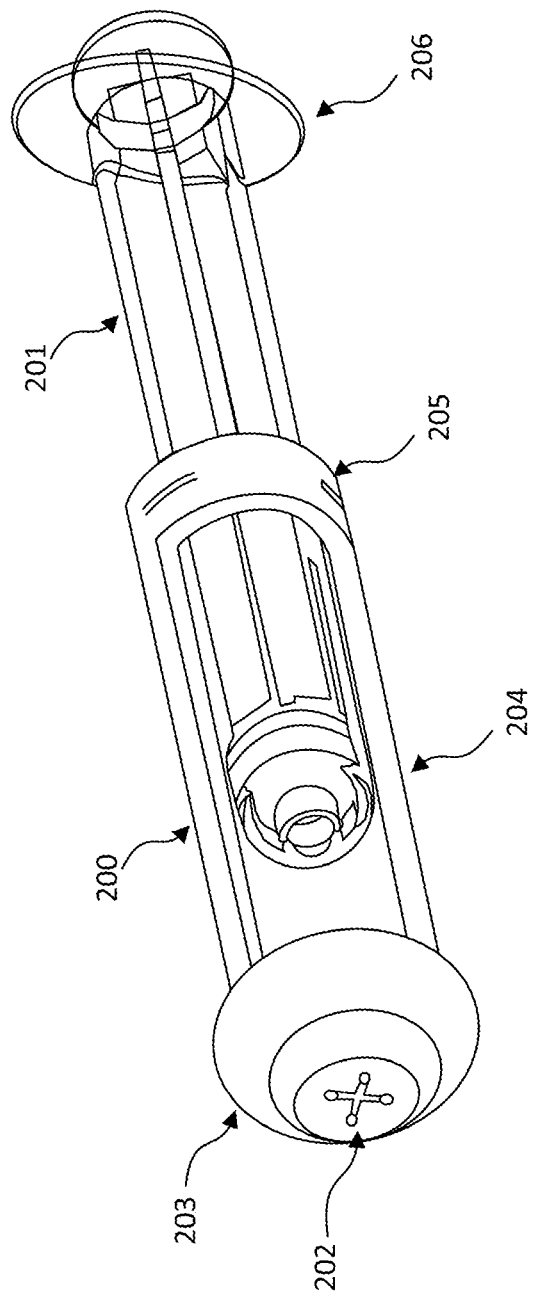
FIG. 2A depicts an exemplary insemination device comprising a fluid controller and a fluid introduction device.

FIG. 2A depicts an insemination device comprising an exemplary fluid controller 200 coupled with a fluid introduction device 201. In the example of FIG. 2A, the fluid controller comprises an orifice 202 arranged relative to the body of the fluid controller. Orifice 202 may facilitate transfer of a fluid (e.g., semen, pharmaceutical fluids, etc.) from the fluid introduction device 201 through the fluid controller 200. As shown in FIG. 2A, a fluid retention structure 203 extends outwardly from at least a portion of the body 204 of the fluid controller 200, wherein body 204 is configured to extend at least partially over the fluid introduction device 201. In some cases, fluid controller 200 may include one or more connectors 205 configured to releasably attach the fluid controller 200 to one or more structures associated with the fluid introduction device 201. For example, in some cases, as will be discussed in more detail in the sections below, connector 205 may include one or more slots, hooks, loops, etc. configured to engage with one or more structures associated with fluid introduction device 201. In the example embodiment of FIG. 2A, the connector 205 includes slots for attaching to protrusions (not shown) associated with fluid introduction device 201. In some cases, the fluid introduction device 201 may include a syringe comprising a barrel flange 206 that includes tabs, protrusions, etc. for interfacing with connector 205.

The disclosed fluid controllers may take many different forms and may be arranged to operate with various types and configurations of fluid introduction devices. In some cases, for example, the fluid controller may be integrated together with the fluid introduction device. In other cases, as noted above, the fluid controller may be formed as a separate component relative to the fluid introduction devices. In such cases, the fluid controller may be used with multiple different types of fluid introduction devices, including, for example, certain syringes, plunger-based devices, or other types of fluid introduction devices (off the shelf or otherwise). In addition to providing a path for fluid flow (e.g., via orifice 202), the disclosed fluid controllers may also include one or more structures aimed at retaining fluid in a volume into which fluid has been introduced (e.g., a vaginal canal or other type of cavity, including body cavities or otherwise).

Figures 2B, 2C, 2D:
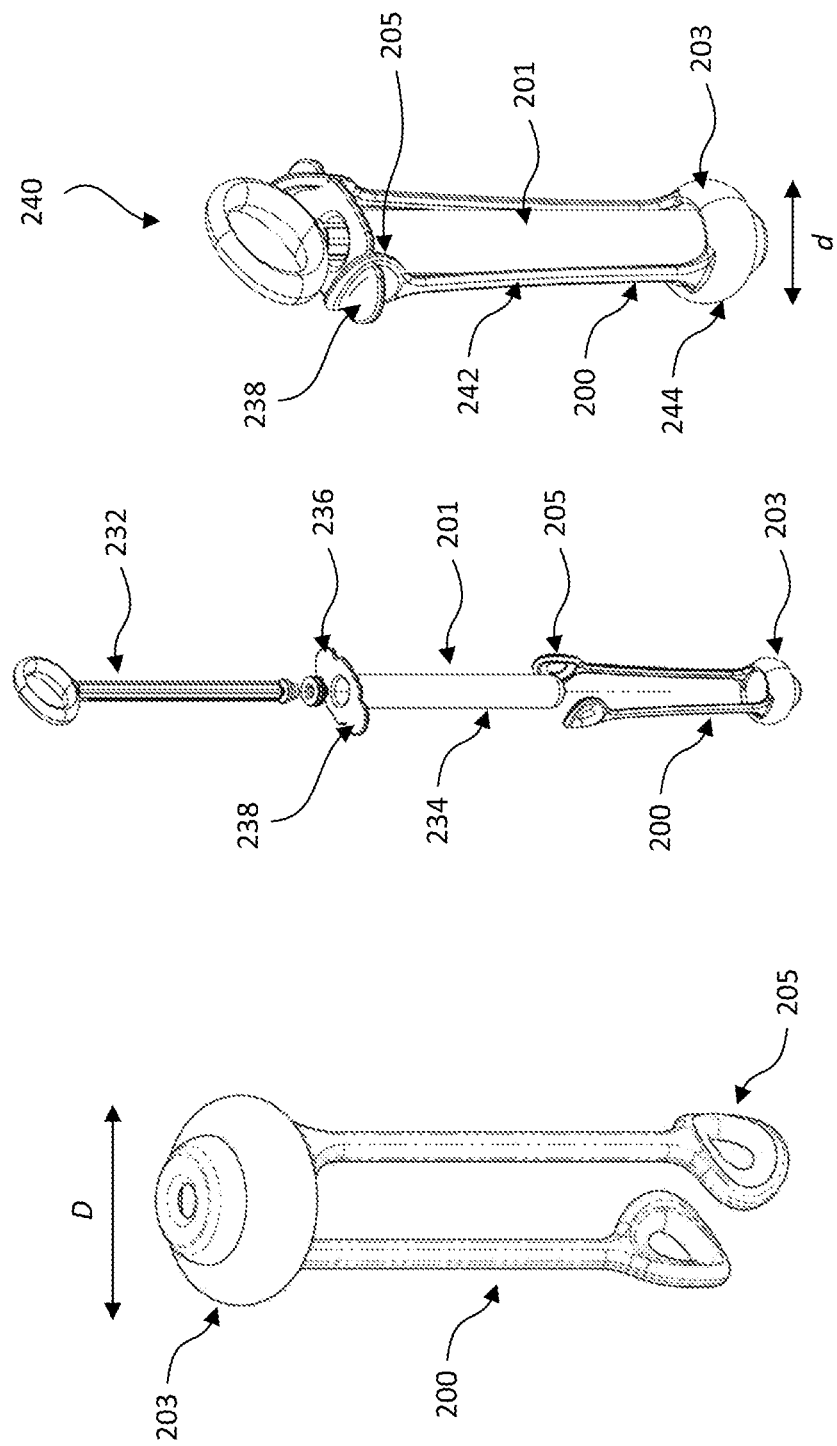
FIG. 2B depicts an exemplary fluid controller.
FIG. 2C depicts an exploded assembly view of an exemplary fluid controller and fluid introduction device.
FIG. 2D depicts an exemplary fluid controller installed on a fluid introduction device.

For example, as shown in the example of FIG. 2B, fluid controller 200 may include a fluid retention structure 203, which may take the form of a plug, shield, flange, etc. to slow or prevent fluid leakage past the fluid retention structure and out of the volume into which the fluid was introduced. Notably, the fluid retention structure may be designed to slow or prevent such fluid leakage whether the fluid controller 200 remains attached to fluid introduction device 201 or whether the fluid controller 200 is detached from fluid introduction device 201 after fluid introduction (e.g., insemination). As will be discussed further below, the fluid controller may include structural features that facilitate detachment of the fluid controller from the fluid introduction device and that allows the fluid introduction device to be separated from the fluid controller without dislodging the fluid controller from a seated location. For example, the fluid introduction device can be detached from the fluid controller and removed from the vaginal canal while the fluid controller remains in the vaginal canal and retains or at least partially retains deposited insemination fluid proximate to the cervix.

In the example of FIG. 2B, fluid controller 200 includes connectors 205 in the shape of rings configured to slip over corresponding protrusions associated with a fluid introduction device 201. FIG. 2C shows an exploded assembly view of a fluid introduction device 201, comprising a body 234, a plunger 232, and a barrel flange 236. Barrel flange 236 includes tabs 238 that extend outwardly from body 234. In this example, the ring-shaped connectors 205 are sized to slip over corresponding tabs 238 (of barrel flange 236) extending from opposite sides of body 234. FIG. 2D provides an isotropic view of fluid controller 200 installed on fluid introduction device 201 to provide (in this particular example) a fluid insemination device 240. It should be noted that device 240 can be used to deposit any type of fluid (e.g., semen, pharmaceuticals, etc.) into a desired volume (e.g., a vaginal cavity or any other type of volume in a body or elsewhere). As shown, fluid controller 200 includes two legs 242 terminated by ring-shaped connectors 205. To install fluid controller 200 on fluid introduction device 201, a head 244 of fluid controller 200 is placed over a fluid depositing end of fluid introduction device 201 (a syringe in this case), and legs 242 are stretched until ring-shaped connectors 205 can be attached to tabs 238 of barrel flange 236.

Figure 15:
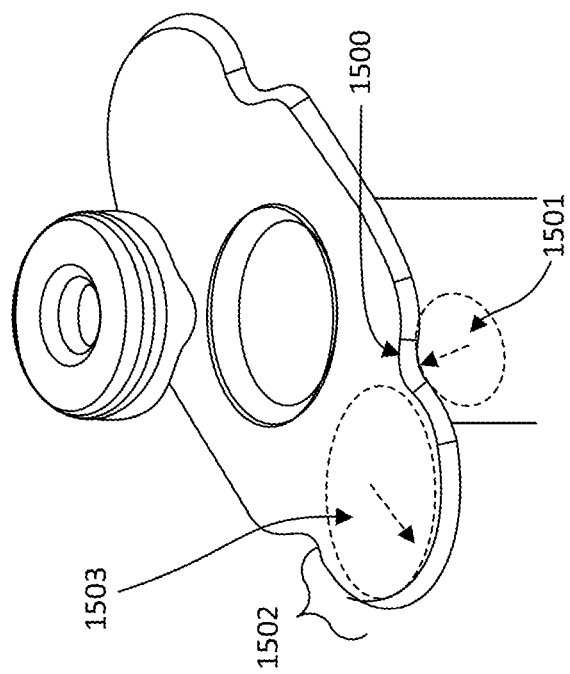
FIG. 15 depicts exemplary barrel flange tab embodiments for attaching a fluid controller to a fluid introduction device.

Tabs of a barrel flange (such as tab 238 shown in FIG. 2C) may have one or more recesses, and these recesses may have various configurations. FIG. 15 depicts an example barrel flange tab showing a recess 1500 having a radius of curvature 1501. Each recess may have a radius of curvature ranging from 0.5 mm to 8 mm. Each recess may be, e.g., circular, oval shaped, square, rectangular, or etc. The length 1502 of each tab may be varied, e.g., from 5 mm to 5 cm, and may have a radius of curvature 1503 ranging from, e.g., 5 mm to 5 cm. The recesses may be configured to receive, e.g., a loop on a connector to connect the fluid controller to the fluid introduction device and allow a user to easily attach and detach the connector from the fluid introduction device. Varying the length 1502 and radii of curvature 1501 and/or 1502 of the barrel flange tabs may promote ease of engagement of the fluid controller connector with the barrel flange, may aid in retaining the connector of the fluid controller on the tab during operation, and also may assist in disengaging the fluid controller connector from the tab to separate the fluid introduction device from the fluid controller after introduction of fluid into a volume. Further, while the barrel flange tabs of the FIG. 1.5 example are shown as each including two recesses 1500 (one on either side of the tab, more or fewer recesses may be included. For example, in some cases, a flange tab may result from forming a single recess 1500 on a barrel flange. In other cases, such as the example of FIG. 15, the barrel flange tab may be provided by forming two recesses 1500 on the barrel flange. In still other examples, the disclosed tabs may be associated with more than two recesses (e.g., a multi-notch tab, a graduated multi-step tab, etc.). The radius of curvature may also extend over a varying angular range. In some cases, the radius may extend over a range of between 30 degrees and 90 degrees (as shown in FIG. 15). In other cases, the angular range may be greater than 90 degrees (e.g., up to 180 degrees or more) to create a notch in the barrel flange. Such a notch may increase the ability of the flange to retain the connector of the fluid controller, but may come at a cost in terms of ease of disengagement of the fluid controller connector from the barrel flange.

Fluid may be loaded into the fluid introduction device (e.g., syringe) 201 before or after the fluid controller 200 is connected to the fluid introduction device 201. In either case, the fluid-loaded insemination device 240 may then be positioned into a vaginal canal. Insemination fluid may then be deposited in the vaginal canal by passing at least a portion of the fluid through the orifice of the fluid controller 200 using plunger 232 of fluid introduction device 201, for example. In some cases, after passing fluid from the fluid introduction device into the vaginal canal, the fluid controller/fluid introduction device assembly may be retained in the vaginal canal (e.g., for a predetermined amount of time). In other cases, however, the fluid controller 200 may be detached from the fluid introduction device 201, and the fluid introduction device may be removed from the vaginal canal while the fluid controller remains in the vaginal canal.

The disclosed fluid controllers may be configured such that attachment of the fluid controller 200 to the fluid introduction device 201 results in a reduction in one or more dimensions associated with the fluid controller, which can aid in introduction of the fluid controller/fluid introduction device assembly into a vaginal canal. For example, the fluid controller 200 may be configured such that a maximal cross-sectional diameter of the fluid retention structure 203 is reduced when the fluid controller 200 is attached to the fluid introduction device 201. That is, stretching the connectors 242 may cause the fluid controller 200 to deform in at least one radial direction. For example, as shown in FIGS. 2B and 2D, stretching of legs 242 such that connectors 205 engage with tabs 238 causes the material of head 244 to also stretch. As a result of attachment of fluid controller 200 to fluid introduction device 201, a diameter D associated with the fluid retention structure 203 in an unstretched state (FIG. 2B) is reduced to a diameter d in a stretched state (FIG. 2D). More specifically, the fluid controller 200 may be characterized by an axial dimension (e.g., length) and a radial dimension (e.g., D/2). While the axial dimension of fluid controller 200 may be increased by attaching fluid controller 200 to fluid introduction device 201, the radial dimension may be decreased.

The fluid retention structure 203 may be configured such that a region at an outer periphery of the fluid retention structure 203 engages with the interior walls of a vaginal canal after introduction of the fluid controller/fluid introduction device assembly into the vaginal canal. Deformation of the fluid retention structure 203 in at least one radial direction, therefore, may aid in the insertion of the insemination device assembly. For example, stretching of connectors 242 may cause the fluid controller 200, including the fluid retention structure 203, to deform (e.g., narrow) in at least one radial direction, which can facilitate introduction of the fluid controller 200 into a vaginal canal.

Deformation of the fluid controller 200 may offer other potential benefits. For example, such stretching and associated deformation can open or change the shape of the orifice (see FIG. 5).

As noted above, in some cases, after depositing fluid from the fluid introduction device 201, through fluid controller 200, and into a volume, the fluid controller 200 may be detached from the fluid introduction device 201. The fluid introduction device may be removed from the vaginal canal while the fluid controller remains in the vaginal canal. Detaching the fluid controller 200 from the fluid introduction device 201 may cause the fluid controller 200 to relax from a deformed state (e.g., a stretched or narrowed state) to an undeformed or at least less deformed state (e.g., a wider state). Relative to the deformed state, the less deformed or undeformed state may more securely engage a vaginal wall to reduce backflow of insemination fluid out of the vaginal canal. For example, in a less deformed or undeformed state, a radial dimension of the fluid retention structure 203 may increase to increase a level of engagement between a vaginal wall and the fluid retention structure 203.

FIG. 3 depicts an exemplary fluid controller (300) wherein attachment of the fluid controller to the fluid introduction device (301→302) causes a reduction in a radial dimension associated with the fluid retention structure (303).

Removal of the fluid introduction device 201 from the vaginal canal may be more comfortable for the subject than maintaining the complete fluid controller/fluid introduction device assembly within the vaginal canal. Further, removal of the fluid introduction device, while leaving the fluid controller in place within the vaginal canal, can promote conception, as the fluid controller may be maintained in place for any suitable period of time (e.g., 10 minutes, 30 minutes, 1 hour, 8 hours, etc.). And while the fluid controller 200 is maintained in the vaginal canal, flowback of insemination fluid past the fluid controller 200 and out of the vaginal canal may be reduced or eliminated, e.g., by the full or partial engagement of the fluid retention structure 203 with the vaginal wall.

Figure 12:
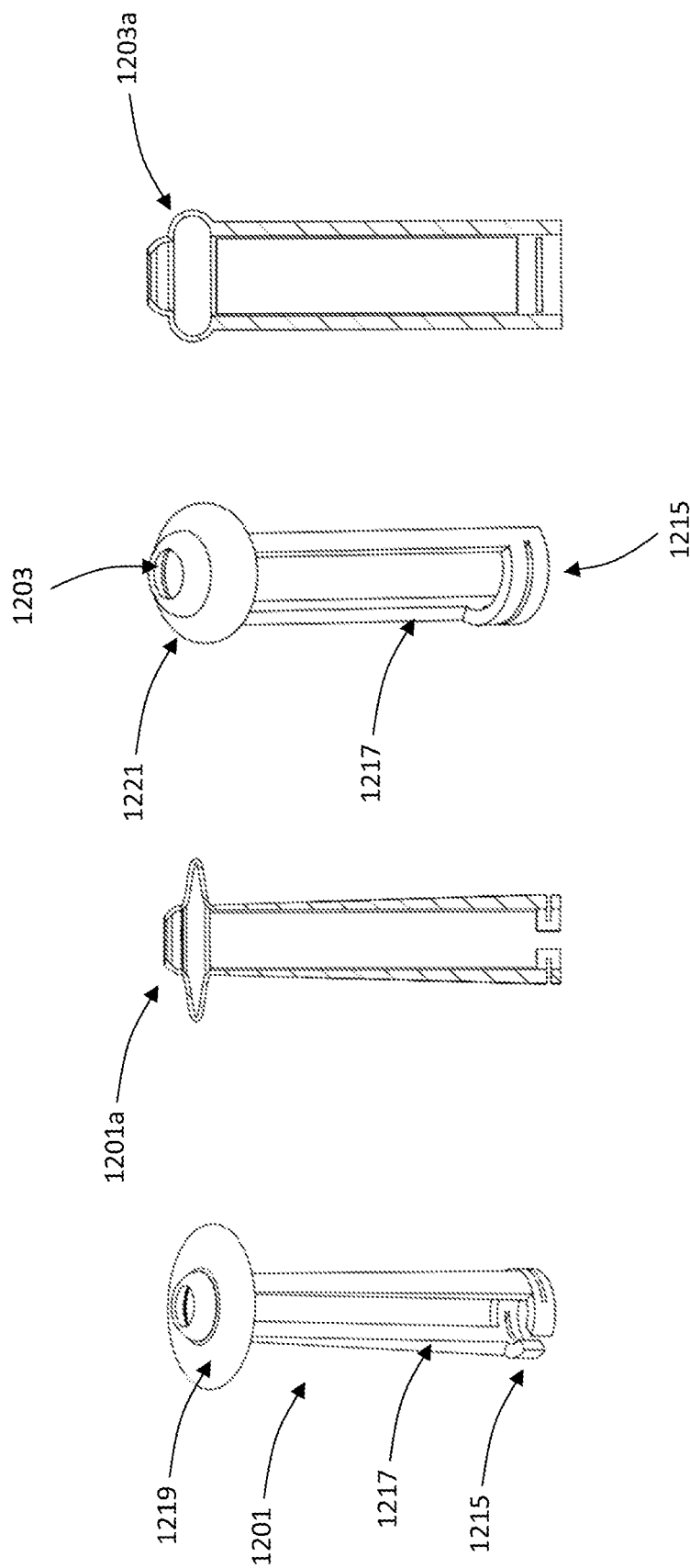
FIG. 12 depicts exemplary fluid controller embodiments.

Various structures may be included on fluid controller 200 and/or fluid introduction device 201 to facilitate removable attachment of the fluid controller 200 to the fluid introduction device 201. For example, connectors 205 may be shaped for quick removal from the barrel flange 236 of a syringe. Such shapes may include rings, as shown in FIG. 2D, or may include recesses, as shown in FIG. 6, 12, or 14, among other shapes. The fluid introduction device may also be fitted with a quick release mechanism or other type of quick release element to encourage disconnection of the fluid controller 200 from the fluid introduction device 201. Such quick release mechanisms may include plungers, winged structures, spring loaded buttons, etc. configured to disengage fluid controller 200 from fluid introduction device 201 (e.g., to dislodge connectors 205 from tabs 238, etc.).

Other aspects of the fluid controller and fluid introduction device may also be configured to facilitate separation of the fluid controller 200 from the fluid introduction device 201. For example, in some cases, the coefficient of friction between the fluid controller and the fluid introduction device may be selected to be less than a known or estimated coefficient of friction between the fluid controller and the vaginal wall. Such relative coefficients of friction may assist in removal of the fluid introduction device from the vaginal canal without also removing the fluid controller from the vaginal canal. It is believed a coefficient of friction between the fluid controller and the vaginal wall that is greater than the coefficient of friction between the fluid controller and the fluid introduction device may aid in removal of the fluid introduction device from the vaginal canal after deposition of the insemination fluid while the fluid controller is maintained in place inside the vaginal canal. In some examples, the fluid controller 200 and fluid introduction device 201 may be fabricated such that an interface between the fluid controller and the fluid introduction device has a lower coefficient of friction than a coefficient of friction between the fluid controller 200 and a vaginal wall. For example, mating surfaces between the fluid controller and the fluid introduction device may be coated with one or more friction-reducing materials (polytetrafluoroethylene (PTFE), etc.). Additionally or alternatively, one or more outer surfaces of fluid controller 200 may be fabricated with textured features, such as ridges, ribs, soft spikes, etc. to discourage slippage of the fluid controller 200 once engaged with a vaginal wall. Such structures/textures may result in a coefficient of friction between the fluid controller 200 and the vaginal wall that is greater than the coefficient of friction between the fluid controller and the fluid introduction device.

Fluid controller 200 may be sized according to the requirements of a particular application. In some embodiments, the fluid controller 200 has a length ranging from 50 mm to 100 mm when not attached to the fluid introduction device 201. In some embodiments, the fluid controller has a length ranging from 60 mm to 90 mm when not attached to the fluid introduction device. In some embodiments, the fluid controller has a length ranging from 70 mm to 90 mm when not attached to the fluid introduction device. In some embodiments, the fluid controller has a length ranging from 75 mm to 85 mm when not attached to the fluid introduction device.

While FIGS. 2B-2D show a fluid retention structure 203 including a dome shape, the fluid retention structures associated with the disclosed fluid controllers may include many different shapes, each offering different performance characteristics. For example, FIG. 9 depicts an exemplary retention structure 400 having four flaps and another exemplary retention structure 401 including eight flaps. In either case, and as a result of the spaces between adjacent flaps, retention structures 400 and 401 are free to deform to a smaller diameter or at least one radial dimension upon introduction into the vaginal canal (402→403).

The disclosed fluid retention structures may have any suitable dimensions. In some embodiments, the fluid retention structure has a maximal cross-sectional diameter ranging from 12 mm to 50 mm when the fluid controller is not attached to the fluid introduction device. In some embodiments, the fluid retention structure has a maximal cross-sectional diameter ranging from 15 mm to 35 mm when the fluid controller is not attached to the fluid introduction device. In some embodiments, the fluid retention structure has a maximal cross-sectional diameter ranging from 20 mm to 30 mm when the fluid controller is not attached to the fluid introduction device.

Further, the disclosed fluid retention structures may be fabricated from materials offering suitable hardness and/or elastic properties. In some embodiments, the fluid retention structure has a Shore A hardness ranging from 0 to 70. In some embodiments, the fluid retention structure has a Shore A hardness ranging from 10 to 70. In some embodiments, the fluid retention structure has a Shore A hardness ranging from 20 to 70. In some embodiments, the fluid retention structure has a Shore A hardness ranging from 30 to 70. In some embodiments, the fluid retention structure has a Shore A hardness ranging from 10 to 60. In some embodiments, the fluid retention structure has a Shore A hardness ranging from 10 to 50. In some embodiments, the fluid retention structure has a Shore A hardness ranging from 0 to 40.

In some embodiments, the fluid retention structure comprises one or more of a flap, a bulb, a plug, or a valve. In some embodiments, the fluid retention structure comprises at least two flaps. In some embodiments, the fluid retention structure is configured to engage the vaginal wall and retain the fluid controller at least partially within the vaginal canal after the fluid introduction device is detached from the fluid controller and removed from the vaginal canal. Without wishing to be bound by theory, it is believed that the fluid retention structure may aid conception by retaining deposited insemination fluid within the vaginal canal after the fluid introduction device is removed.

In some embodiments, when the vaginal walls are allowed to collapse onto an unsupported fluid retention structure (e.g., after detachment and removal of a fluid introduction device), the fluid retention structure may flatten in at least one radial direction and widen in another radial direction. Allowing the fluid retention structure to deform to the contours of the vaginal wall may result in an improved seal between the fluid retention structure and the vaginal walls.

Figure 4:
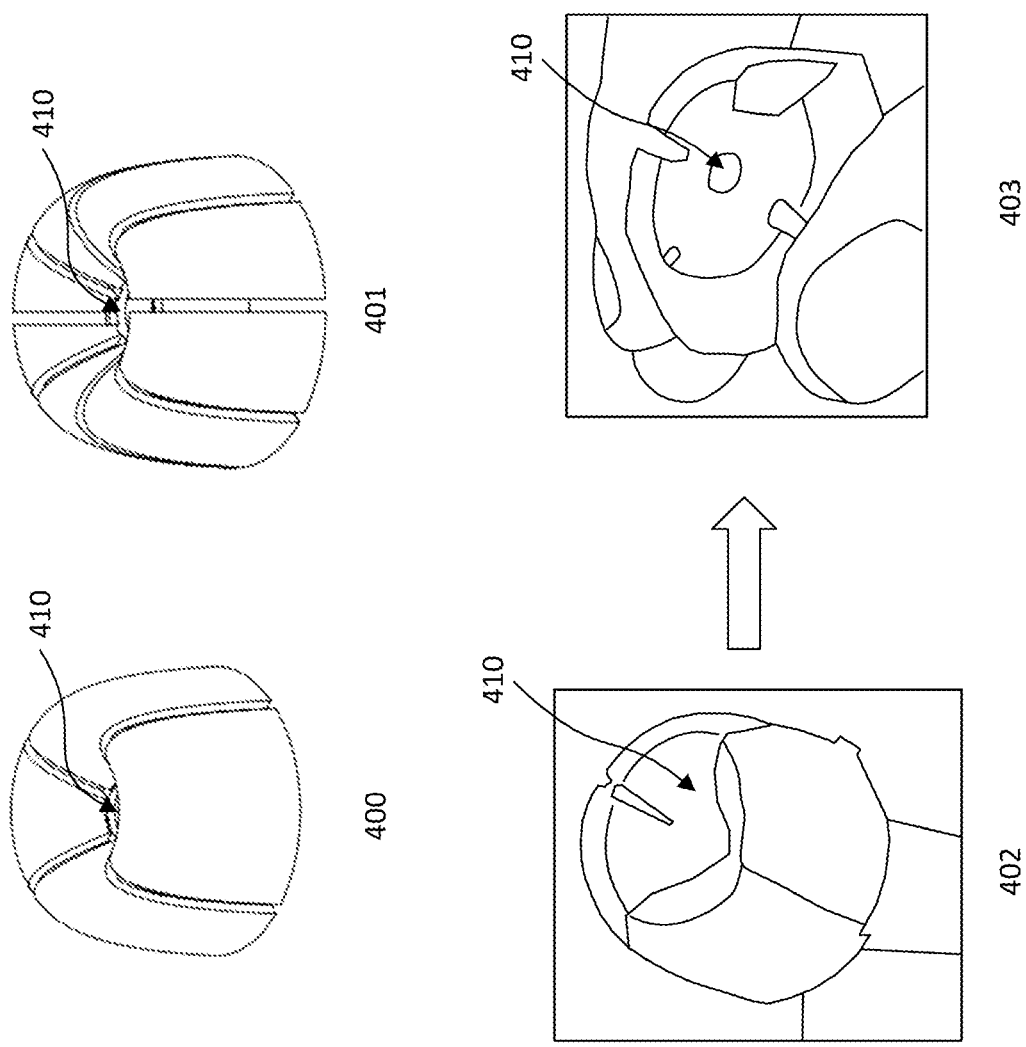
FIG. 4 depicts exemplary fluid retention structure embodiments.

In some embodiments, the fluid retention structure includes an orifice configured to allow the passage of an insemination fluid from the fluid introduction device through the fluid controller. For example, returning to FIG. 4, an orifice 410 is shown at a center of the fluid retention structures 400 and 401. The orifice may be configured with a variety of shapes.

FIG. 5 depicts a fluid controller 520 in different views, including a side view 501, a cross sectional view 502, and an isotropic view 503. As shown, fluid controller 520 includes a single slit orifice 504, which is configured such that when the fluid controller is attached to the fluid introduction device, the slit is more open than when the fluid controller is not attached to the fluid introduction device. For example, the single slit orifice 504 may be configured to open wider when head 510 is under tension (e.g., when legs 512 are stretched to fit fluid controller 520 to a fluid introduction device 506).

FIG. 6 depicts different orifice configurations according to exemplary disclosed embodiments. For example, in a first configuration, a fluid controller 601 may include a circular opening orifice 603. In another exemplary embodiment, a fluid controller 605 may include a cross-shaped orifice 607. The cross-shaped orifice 607 may include any arrangement of at least two intersecting slots (e.g., intersecting at perpendicular or non-perpendicular angles). The slits included in a cross-shaped orifice may include round openings at the ends of the slits, as represented by orifice 610, or may include slits of uniform widths without rounded ends, as represented by orifice 612. The number of slits, the slit crossing angles, and the slit shapes may all influence the degree to which the orifice opens in response to installation of a fluid controller onto a fluid introduction device. These parameters may also influence the flow of fluid through the orifice.

Figure 7:
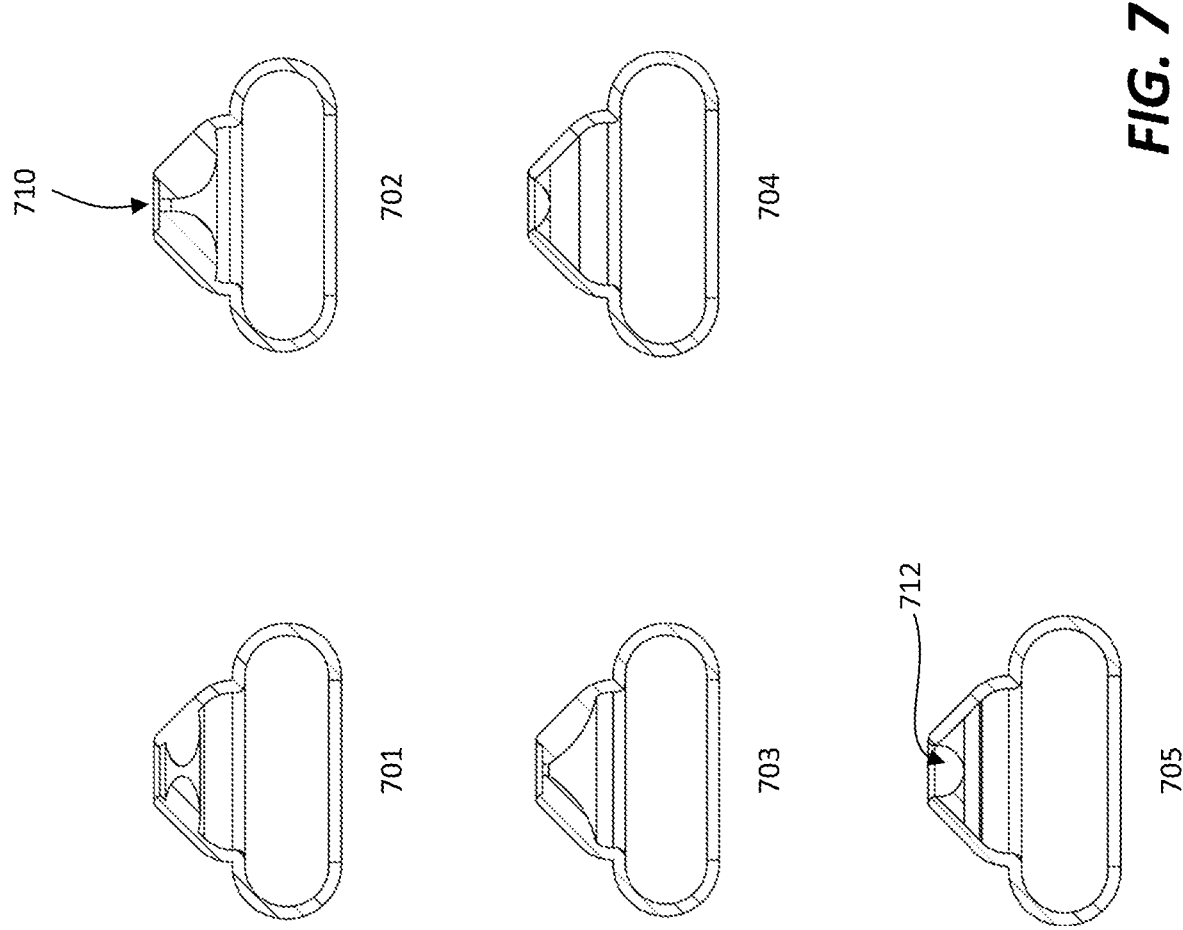
FIG. 7 depicts cross-sectional views of exemplary fluid retention structures and orifice embodiments.

FIG. 7 depicts various fluid retention structures 701 to 705 having different cross-sections. For example, fluid retention structures 701, 702, and 703 all include inner walls that in cross-section exhibit a convex shape. This convex shape may assist in causing an orifice, such as orifice 710 to open in response to contact between the inner walls of the fluid retention structure and a fluid introduction device (e.g., as a result of sliding a fluid controller onto the fluid retention device and stretching the fluid controller into place). Fluid retention structures 704 and 705, on the other hand, include inner walls having concave cross-sections. Such structures may assist in causing an orifice, such as orifice 712, to widen in response to tension placed on the fluid retention structure (e.g., by stretching connectors attached to the fluid retention structure, as shown in FIG. 2D).

Figure 8B:
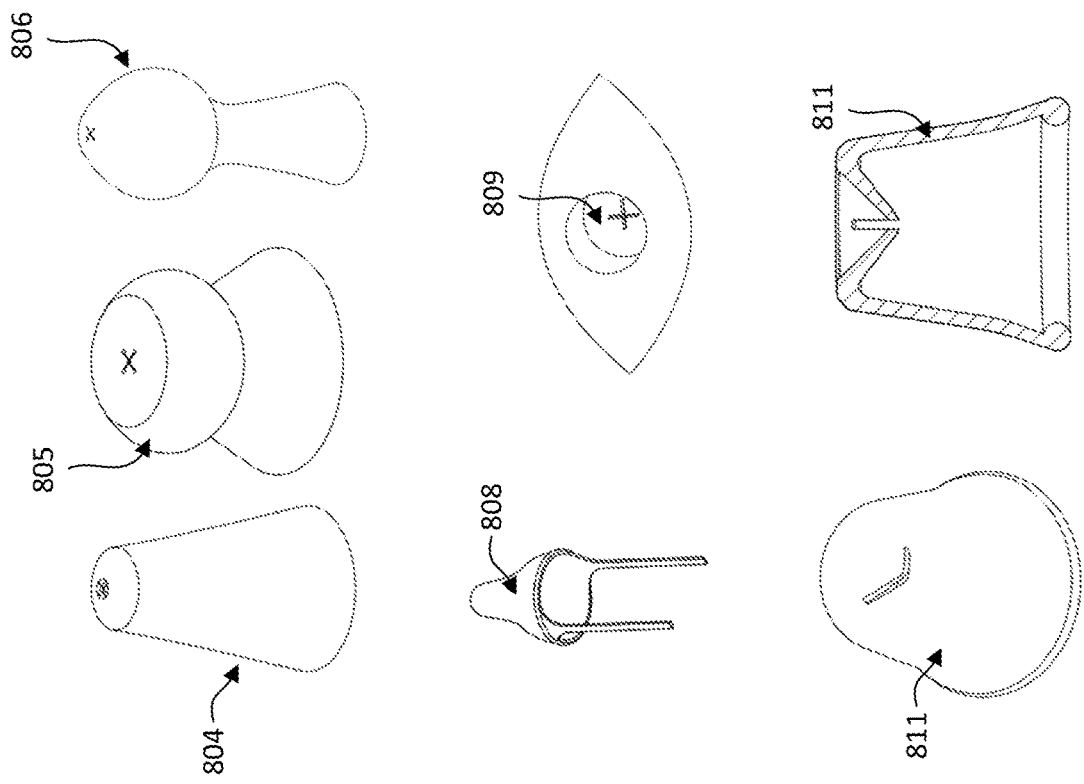
FIG. 8B depicts exemplary fluid retention structure embodiments.
Figure 8A:
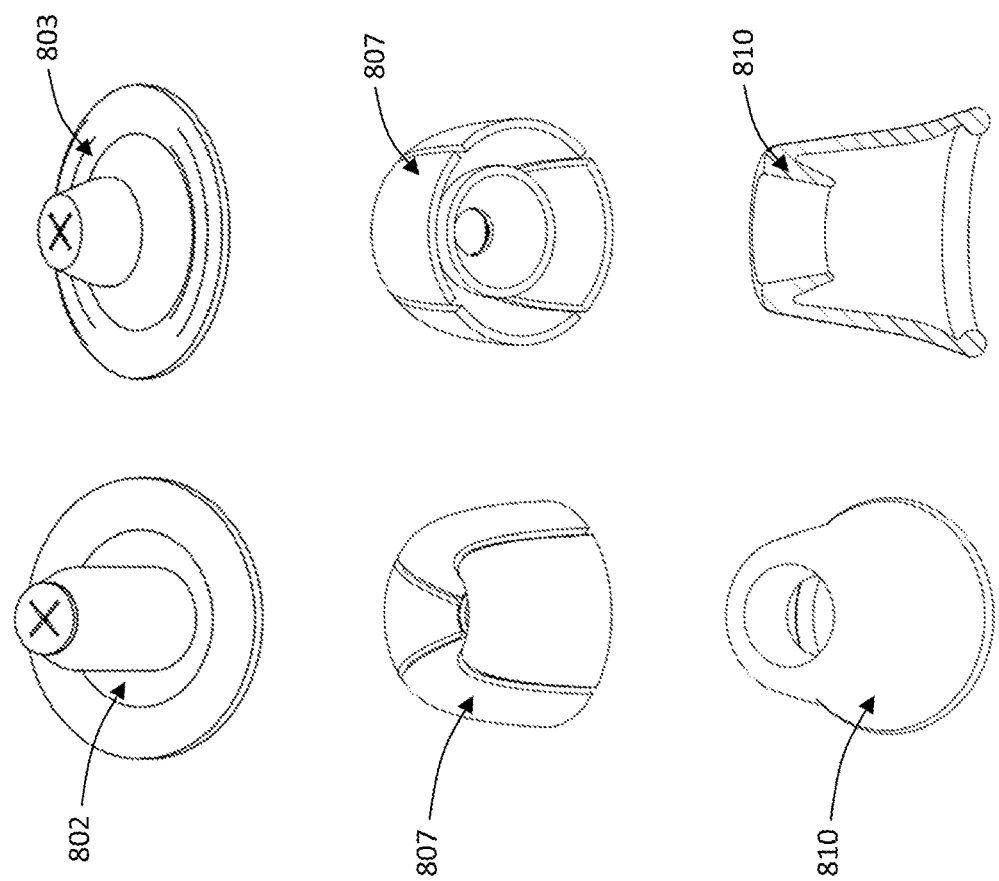
FIG. 8A depicts exemplary fluid retention structure embodiments.

FIGS. 8A and 8B depict a variety of fluid retention structures and orifice embodiments. For example, in some cases a fluid retention structure included on the disclosed fluid controllers may include a tubular interface 802, a trapezium interface 803, a cone interface 804, various spherical interfaces 805 and 806, a dome interface 807, an irregular interface 808, a cylinder interface 809, an inverted cone interface 810, or a bicuspid valve interface 811.

FIG. 9 depicts additional fluid retention structure and orifice embodiments. Such embodiments may include, for example, a concave trumpet shaped embodiment 901, a convex trumpet shaped embodiment 902, an isometric embodiment (903 top view and 904 bottom view), an isometric embodiment with elongated sides 905, a cone embodiment 906, and a rugby ball (elongated) embodiment 907.

Figure 10:
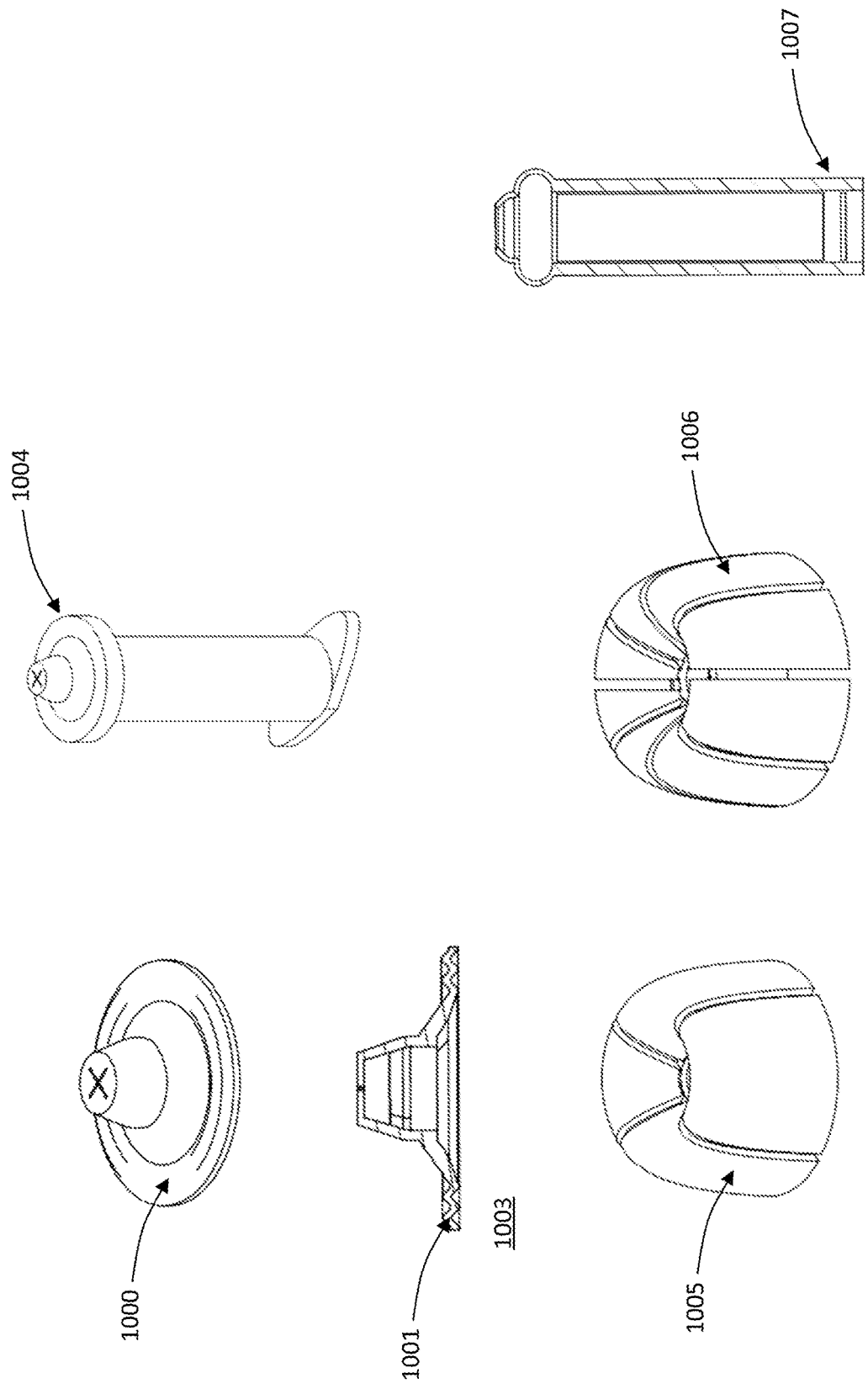
FIG. 10 depicts exemplary fluid retention structure embodiments.
Figure 11:
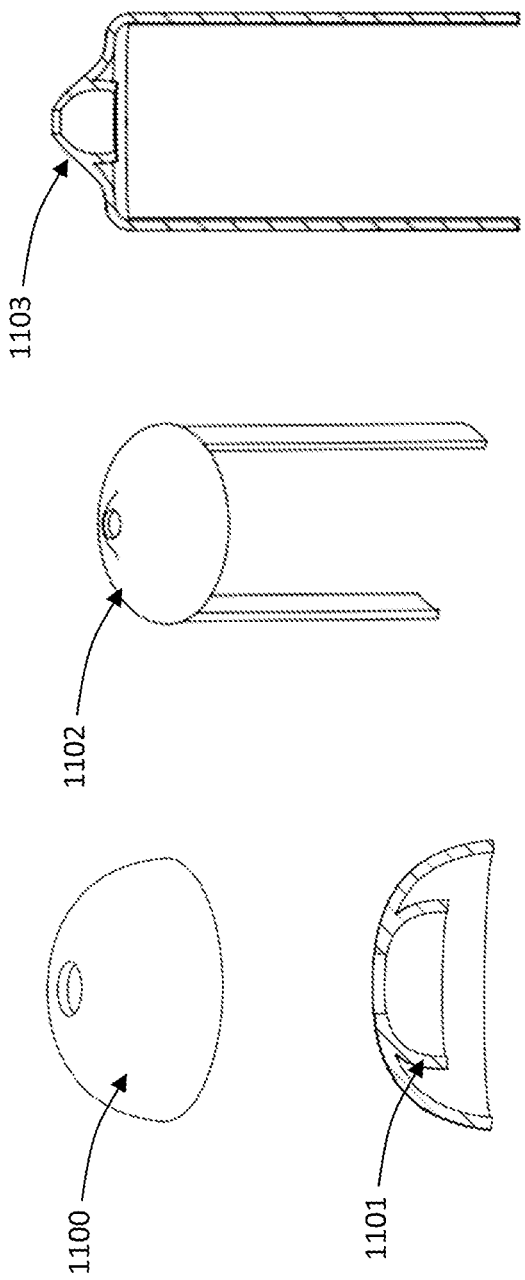
FIG. 11 depicts exemplary fluid retention structure embodiments.

FIG. 10 depicts still further fluid retention structure and orifice embodiments. As shown in FIG. 10, exemplary fluid retention structures may include a trumpet shaped retention structure 1000 with a wavy flange 1001 shown in cross-section 1003. Exemplary fluid retention structures may also include a disc shaped embodiment 1004, a four-flapped embodiment 1005, an eight-flapped embodiment 1006, and a kirigami embodiment 1007. FIG. 11 depicts additional exemplary fluid retention structure and orifice embodiments, including a domed embodiment 1100 having an internal sub-dome interface 1101, which may be configured to communicate with a tip end of a fluid introduction device, such as a syringe. Similarly, fluid retention structure 1102 may include a bell-shaped outer structure and a pseudo-spherical internal interface element 1103, which may be configured to communicate with a tip end of a fluid introduction device.

FIG. 12 depicts additional examples of fluid controller configurations. For example, FIG. 12 shows a fluid controller 1201 (1201a in cross section) and a fluid controller 1203 (1203a in cross section). Similar to other disclosed fluid controllers described above, fluid controllers 1201 and 1203 both include at least one connector 1215 including one or more grooves, slots, or another type of recess, hole, etc. for attaching the fluid controller to a fluid introduction device (e.g., a syringe). Fluid controllers 1201 and 1203 also include legs 1217 that join connectors 1215 with a corresponding fluid retention structure—namely fluid retention structure 1219 of fluid controller 1201 and fluid retention structure 1221 of fluid controller 1203. It should be noted that the disclosed fluid controllers may include various different connector configurations. For example, fluid controller 1201 includes two connectors 1215 located at the ends of respective legs 1217. On the other hand, fluid controller 1203 includes only one connector 1215 spanning between two legs 1217.

In these example, fluid retention structures 1219 and 1221 have substantially symmetrical cross sections (a bellows shaped cross section for fluid retention structure 1219 and an oval cross section exhibited by fluid retention structure 1221). Other shapes are also possible. In these examples, and similar to the fluid retention structures described above, applying tension to fluid retention structures 1219 or 1221, e.g., by applying tension to legs 1217, causes a change in shape of the fluid retention structures 1219 and 1221. For example, an axial dimension (along the length of the fluid controllers) may increase while a radial dimension (e.g., associated with a diameter of fluid retention structures 1219 and 1221) may decrease. As with the fluid retention structures described above, such a decrease in radial dimension can assist in the introduction of the fluid controller within a vaginal canal.

The configuration of fluid retention structures 1219 or 1221 may offer certain advantages. For example, in view of their symmetric configuration, engagement of the fluid retention structures 1219 or 1221 may be established as the respective fluid controller is moved in a direction toward the cervix, but can be similarly maintained even if the respective fluid controller is moved toward a vaginal opening (e.g., before or after detachment of the respective fluid controller from a fluid introduction device).

Figure 13:
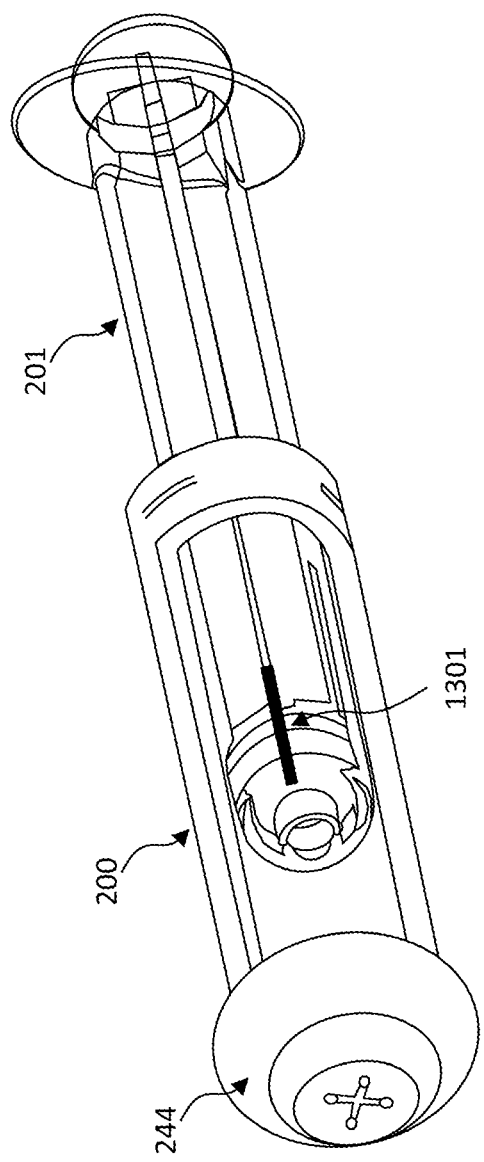
FIG. 13 depicts exemplary an alignment structure for assisting in attaching a fluid controller to a fluid introduction device.

Various structures may be included on the fluid controller and/or the fluid introduction device to assist in attaching the fluid controller to the fluid introduction device. For example, as shown in FIG. 13, fluid introduction device 201 may include an alignment guide 1301 to assist in aligning fluid controller 200 with fluid introduction device 201 during assembly. In some cases, alignment guide 1301 may include a rib, wing, post (or other types of protrusions). In other cases, alignment guide 1301 may include a groove or other types of recesses. Fluid controller 200 may include a mating structure (e.g., a corresponding groove, detent, protrusion, etc.) (not shown) configured to mate with alignment guide 1301. In some cases, the mating structure may be included on fluid controller 200 on an underside of head 244.

The disclosed fluid controllers may include varied structural features. For example, the disclosed fluid controllers (e.g., fluid controller 200) may include various numbers and arrangements of legs, connectors, and fluid retention structures. A body of the fluid controller may also have various shapes, such as a cylindrical body, a partial cylinder, various leg shapes, etc. For example, the fluid controller may have a cylindrical body and/or a partial cylinder body configured to fit over the body of a syringe.

The disclosed connectors may also be configured with a variety of shapes for use in connecting a fluid controller to a fluid introduction device. As noted above, the connectors may include partial slots, full slots, holes, loops, notches, hooks, ridges, rings, or any other structure that can be used to attach a fluid controller to a corresponding structure associated with a fluid introduction device (e.g., tabs on a barrel flange, hooks, pins, etc. on a syringe or other type of fluid introduction device). Connectors may be a part of the fluid controller and/or attached to the fluid controller.

FIG. 14 depicts various exemplary connector embodiments. Embodiments include, e.g., an enclosed opening 1402, a slotted opening 1403, a double slotted opening 1404 (also 1406), and two half circle connections with no openings 1405 for fitting over, e.g., a syringe barrel flange. Additional features may include a shoulder section 1401 for relieving stress and reducing a risk of tearing of a connector leg 1410 from head 1412.

Regarding additional options, in some embodiments, the fluid controller may include one or two elongated elements (e.g., legs 1410) extending from a fluid retention structure associated with head 1412 to one or more connector elements (e.g., 1402-1406 or any other type of connector).

The fluid controller may be fabricated using a variety of materials and/or combinations of materials. For example, the fluid controller may comprise silicone. In some embodiments, the fluid controller comprises from 10 weight percent to 100 weight percent silicone by total weight of the fluid controller. In some embodiments, the fluid controller comprises from 20 weight percent to 100 weight percent silicone by total weight of the fluid controller. In some embodiments, the fluid controller comprises from 30 weight percent to 100 weight percent silicone by total weight of the fluid controller. In some embodiments, the fluid controller comprises from 40 weight percent to 100 weight percent silicone by total weight of the fluid controller. In some embodiments, the fluid controller comprises from 50 weight percent to 100 weight percent silicone by total weight of the fluid controller. In some embodiments, the fluid controller comprises from 60 weight percent to 100 weight percent silicone by total weight of the fluid controller. In some embodiments, the fluid controller comprises from 70 weight percent to 100 weight percent silicone by total weight of the fluid controller. In some embodiments, the fluid controller comprises from 80 weight percent to 100 weight percent silicone by total weight of the fluid controller. In some embodiments, the fluid controller comprises from 90 weight percent to 100 weight percent silicone by total weight of the fluid controller. In some embodiments, the fluid controller comprises from 10 weight percent to 90 weight percent silicone by total weight of the fluid controller. In some embodiments, the fluid controller comprises from 10 weight percent to 80 weight percent silicone by total weight of the fluid controller. In some embodiments, the fluid controller comprises from 10 weight percent to 70 weight percent silicone by total weight of the fluid controller. In some embodiments, the fluid controller comprises from 10 weight percent to 60 weight percent silicone by total weight of the fluid controller. In some embodiments, the fluid controller comprises from 10 weight percent to 50 weight percent silicone by total weight of the fluid controller. In some embodiments, the fluid controller comprises from 30 weight percent to 70 weight percent silicone by total weight of the fluid controller. In some embodiments, the fluid controller comprises from 40 weight percent to 60 weight percent silicone by total weight of the fluid controller.

The fluid controller may be fabricated using a variety of materials and/or combinations of materials. For example, at least a portion of the fluid controller comprises a thermally responsive material configured to change shape or color when at least partially within the vaginal canal. The shape change may aid conception by improving fluid retention within the vaginal canal and the color change may improve the ease of use and/or user experience.

In some cases, at least a portion of the fluid controller comprises a pH responsive material configured to change shape or color when at least partially within the vaginal canal. The shape change may aid conception by improving fluid retention within the vaginal canal and color change may improve the ease of use, indicate suitability of the pH for enhanced conception, and/or user experience. The fluid controller may change its shape in response to pH or temperature and may be configured to actuate and bring semen closer to the cervix when the fluid controller is positioned within the vaginal canal.

At least a portion of the fluid controller may comprise a moisture responsive material configured to change shape or color after introduction at least partially within the vaginal canal. The shape change may aid conception by improving fluid retention within the vaginal canal and color change may improve the ease of use and/or user experience.

In some embodiments, the fluid controller is a monolithic material. For example, the fluid controller may be molded and/or 3D printed silicone.

The disclosed fluid controllers and fluid introduction devices may be used to deliver various different fluids to one or more volumes. For example, in some cases, the fluid includes semen. In other cases, the fluid includes at least one pharmaceutical product, such as progesterone.

As used herein, the term "about" refers to a ±5% of the stated number.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, such as, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub range within the stated ranges in different embodiments of the disclosure, unless the context clearly dictates otherwise.

Those of ordinary skill in the art will recognize or be able to ascertain using no more than routine experimentation, many equivalents to the specific embodiments of the disclosure described herein. Such equivalents are intended to be encompassed by the following claims.

What is claimed is:

1. A fluid controller configured for removable attachment to a fluid introduction device, wherein the fluid controller comprises:
   a body configured to extend at least partially over the fluid introduction device;
   an orifice arranged relative to the body to facilitate transfer of a fluid from the fluid introduction device through the fluid controller;
   a fluid retention structure extending outwardly from at least a portion of the body, wherein the fluid retention structure is configured to engage with a wall of a vaginal canal and inhibit a flow of the fluid from the vaginal canal, wherein the fluid retention structure is configured such that attachment of the fluid controller to the fluid introduction device causes a reduction in at least one dimension associated with the fluid retention structure; and
   at least one connector configured to releasably attach the fluid controller to the fluid introduction device.

2. The fluid controller of claim 1, wherein the at least one dimension includes a radial dimension.

3. The fluid controller of claim 1, wherein the at least one connector is further configured such that the fluid controller can be detached from the fluid introduction device after insertion into the vaginal canal and the fluid introduction device can be removed from the vaginal canal without removal of the fluid controller from the vaginal canal.

4. The fluid controller of claim 1, wherein the fluid retention structure is configured to expand in at least one dimension upon detachment of the fluid controller from the fluid introduction device.

5. The fluid controller of claim 1, wherein the fluid introduction device comprises a syringe.

6. The fluid controller of claim 1, wherein the fluid retention structure has a maximal cross-sectional diameter ranging from 12 mm to 50 mm when the fluid controller is not attached to the fluid introduction device.

7. The fluid controller of claim 6, wherein the fluid controller is configured such that the maximal cross-sectional diameter of the fluid retention structure is reduced when the fluid controller is attached to the fluid introduction device.

8. The fluid controller of claim 1, wherein the fluid retention structure has a Shore A hardness ranging from 0 to 70.

9. The fluid controller of claim 1, wherein the fluid retention structure comprises one or more of a flap, a bulb, a plug, or a valve.

10. The fluid controller of claim 1, wherein the fluid retention structure comprises a plug.

11. The fluid controller of claim 1, wherein the fluid retention structure comprises at least two flaps.

12. The fluid controller of claim 1, wherein the at least one connector comprises a loop.

13. The fluid controller of claim 1, wherein the at least one connector is configured to receive a protrusion associated with the fluid introduction device.

14. The fluid controller of claim 1, wherein the fluid controller comprises silicone.

15. The fluid controller of claim 1, wherein the fluid controller comprises from 10 weight percent to 100 weight percent silicone by total weight of the fluid controller.

16. The fluid controller of claim 1, wherein the fluid retention structure is configured to engage the vaginal wall and retain the fluid controller at least partially within the vaginal canal after the fluid introduction device is detached from the fluid controller and removed from the vaginal canal.

17. The fluid controller of claim 1, wherein a coefficient of friction between the fluid controller and the vaginal wall is greater than a coefficient of friction between the fluid controller and the fluid introduction device.

18. The fluid controller of claim 1, wherein the orifice comprises at least two intersecting slots.

19. The fluid controller of claim 1, wherein the at least one connector comprises at least one elastic segment configured to stretch when the fluid controller is attached to the fluid introduction device.

20. The fluid controller of claim 1, wherein at least a portion of the fluid controller comprises a thermally responsive material configured to change shape or color when at least partially within the vaginal canal.

21. The fluid controller of claim 1, wherein at least a portion of the fluid controller comprises a pH responsive material configured to change shape or color when at least partially within the vaginal canal.

22. The fluid controller of claim 1, wherein at least a portion of the fluid controller comprises a moisture responsive material configured to change shape or color after introduction at least partially within the vaginal canal.

23. The fluid controller of claim 1, wherein the fluid introduction device is a syringe comprising a barrel flange, and the at least one connector is configured to removably attach to a portion of the barrel flange.

24. The fluid controller of claim 23, wherein the barrel flange includes one or more recesses having a radius of curvature ranging from 0.5 mm to 8 mm, and wherein the at least one connector is configured to removably attach to one or more of the recesses.

25. The fluid controller of claim 1, further including a quick release element configured to facilitate detachment of the fluid controller from the fluid introduction device.

26. The fluid controller of claim 1, further including one or more alignment guides configured to orient the fluid controller relative to the fluid introduction device.

27. The fluid controller of claim 1, wherein the fluid includes semen.

28. The fluid controller of claim 1, wherein the fluid includes at least one pharmaceutical product, and wherein the at least one pharmaceutical product includes progesterone.

29. The fluid controller of claim 1, wherein the orifice is a single slit and the orifice is configured to open wider when the fluid controller is attached to the fluid introduction device than when the fluid controller is not attached to the fluid introduction device, and wherein the orifice is configured to open wider when the at least one connector is in tension.

30. A fluid controller configured for removable attachment to a fluid introduction device, wherein the fluid controller comprises:
a body configured to extend at least partially over the fluid introduction device;
an orifice arranged relative to the body to facilitate transfer of a fluid from the fluid introduction device through the fluid controller;
a fluid retention structure extending outwardly from at least a portion of the body, wherein the fluid retention structure is configured to engage with a wall of a vaginal canal and inhibit a flow of the fluid from the vaginal canal, wherein the fluid retention structure is configured to expand in at least one dimension upon detachment of the fluid controller from the fluid introduction device; and
at least one connector configured to releasably attach the fluid controller to the fluid introduction device.

31. A fluid controller configured for removable attachment to a fluid introduction device, wherein the fluid controller comprises:
a body configured to extend at least partially over the fluid introduction device;
an orifice arranged relative to the body to facilitate transfer of a fluid from the fluid introduction device through the fluid controller;
a fluid retention structure extending outwardly from at least a portion of the body, wherein the fluid retention structure is configured to engage with a wall of a vaginal canal and inhibit a flow of the fluid from the vaginal canal; and
at least one connector being connected to the fluid retention structure by at least one leg extending from the fluid retention structure, wherein the at least one connector is configured to releasably attach the fluid controller to the fluid introduction device.

32. The fluid controller of claim 31, wherein the at least one leg terminates at the at least one connector.

33. The fluid controller of claim 31, wherein the at least one connector is configured to mate with a tab shaped protrusion associated with the fluid introduction device to releasably attach the fluid controller to the fluid introduction device.

34. The fluid controller of claim 31, wherein the at least one connector is ring-shaped and configured to attach to a tab shaped protrusion associated with the fluid introduction device.

35. The fluid controller of claim 31, wherein the fluid introduction device includes a syringe.

36. The fluid controller of claim 31, wherein the at least one leg is configured to extend from the fluid retention structure toward an opening of the vaginal canal during use.

37. The fluid controller of claim 31, wherein the at least one leg is configured to be stretched to attach the fluid controller to the fluid introduction device, causing tension to be applied to the fluid retention structure.

38. The fluid controller of claim 31, wherein the at least one leg is elastic.

39. The fluid controller of claim 31, wherein the at least one leg is configured to be stretched when the fluid controller is attached to the fluid introduction device.

* * * * *